(12) United States Patent
Knudsen et al.

(10) Patent No.: US 11,033,684 B2
(45) Date of Patent: Jun. 15, 2021

(54) SINGLE-USE AUTO-INJECTOR

(71) Applicant: AMGEN INC., Thousand Oaks, CA (US)

(72) Inventors: Hans Stenberg Knudsen, Gentofte (DK); Christian Plambech, Soeborg (DK); Rasmus Øhlenschlæger, Kobenhavn V (DK); Jørgen Jørgensen, Gentofte (DK)

(73) Assignee: AMGEN INC., Thousand Oaks, CA (US)

( * ) Notice: Subject to any disclaimer, the term of this patent is extended or adjusted under 35 U.S.C. 154(b) by 249 days.

(21) Appl. No.: 15/762,939

(22) PCT Filed: Oct. 28, 2016

(86) PCT No.: PCT/EP2016/076156
§ 371 (c)(1),
(2) Date: Mar. 23, 2018

(87) PCT Pub. No.: WO2017/072333
PCT Pub. Date: May 4, 2017

(65) Prior Publication Data
US 2018/0304014 A1    Oct. 25, 2018

(30) Foreign Application Priority Data

Oct. 28, 2015    (EP) .................................... 15191929

(51) Int. Cl.
*A61M 5/20*    (2006.01)
*A61M 5/145*    (2006.01)
(Continued)

(52) U.S. Cl.
CPC ........ *A61M 5/2033* (2013.01); *A61M 5/1454* (2013.01); *A61M 5/3204* (2013.01);
(Continued)

(58) Field of Classification Search
CPC .. A61M 5/2033; A61M 5/326; A61M 5/3204; A61M 5/1454; A61M 2005/3267;
(Continued)

(56) References Cited

U.S. PATENT DOCUMENTS

| | | | |
|---|---|---|---|
| 2002/0004651 A1* | 1/2002 | Ljunggreen | A61M 5/31501 604/218 |
| 2002/0007154 A1* | 1/2002 | Hansen | A61M 5/20 604/207 |

(Continued)

FOREIGN PATENT DOCUMENTS

| | | |
|---|---|---|
| JP | 2014-515669 A | 7/2014 |
| WO | WO-2010/112377 A1 | 10/2010 |

(Continued)

OTHER PUBLICATIONS

International Search Report and Written Opinion for International Application No. PCT/EP2016/076156, dated Apr. 18, 2017.

(Continued)

*Primary Examiner* — Tiffany Legette
(74) *Attorney, Agent, or Firm* — Marshall, Gerstein & Borun LLP

(57) ABSTRACT

A single-use auto-injector includes a housing and a dosing unit in at least part of the housing. The dosing unit includes a needle, a drug container with drug, a piston movable in the container, a first mechanical power supply for moving the piston to deliver the drug, an activation mechanism, and a mechanical escapement mechanism for controlling the movement of the piston. The auto-injector has a first state in which the needle is protected from needle damage or contamination, a second state in which the needle is ready to penetrate a human body, a third state in which the needle has penetrated the human body and is ready to dose, and a fourth state in which the needle is shielded to avoid unintended needle sticks. A second mechanical power supply is config- (Continued)

ured to shift state of the auto-injector from the third state to the fourth state.

19 Claims, 12 Drawing Sheets

(51) Int. Cl.
*A61M 5/32* (2006.01)
*A61M 5/142* (2006.01)
*A61M 5/315* (2006.01)
(52) U.S. Cl.
CPC ... *A61M 5/326* (2013.01); *A61M 2005/14256* (2013.01); *A61M 2005/14506* (2013.01); *A61M 2005/206* (2013.01); *A61M 2005/31518* (2013.01); *A61M 2005/3267* (2013.01)
(58) Field of Classification Search
CPC .. A61M 2005/31518; A61M 2005/206; A61M 2005/14506; A61M 2005/14256; A61M 5/3257; A61M 5/3243; A61M 2005/2013; A61M 2005/2026; A61M 5/208; A61M 2005/3152; A61M 5/31558; A61M 5/31575; A61M 5/3158
See application file for complete search history.

(56) References Cited

U.S. PATENT DOCUMENTS

| | | | |
|---|---|---|---|
| 2005/0197625 A1* | 9/2005 | Haueter | A61M 5/1454 604/131 |
| 2008/0154200 A1* | 6/2008 | Lesch | A61M 5/46 604/135 |
| 2011/0196311 A1* | 8/2011 | Bicknell | A61M 5/3204 604/198 |
| 2013/0138049 A1* | 5/2013 | Kemp | A61M 5/2033 604/197 |
| 2013/0211330 A1* | 8/2013 | Pedersen | A61M 5/2033 604/111 |
| 2014/0148784 A1 | 5/2014 | Anderson et al. | |

FOREIGN PATENT DOCUMENTS

| | | |
|---|---|---|
| WO | WO-2011/101376 A1 | 8/2011 |
| WO | WO-2014060563 A2 | 4/2014 |
| WO | WO-2014/108494 A1 | 7/2014 |

OTHER PUBLICATIONS

Japanese Patent Application No. 2018-518694, Office Action, dated Sep. 15, 2020.

* cited by examiner

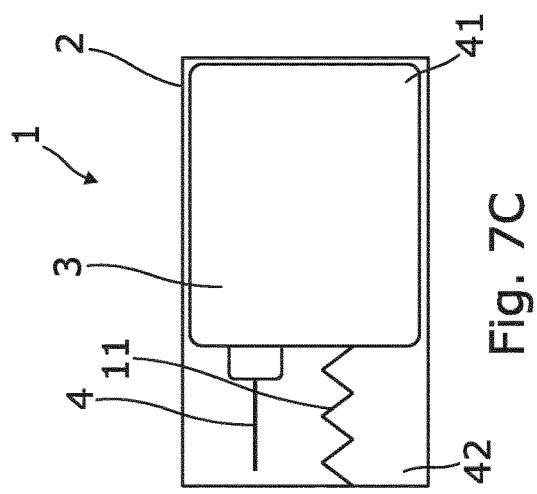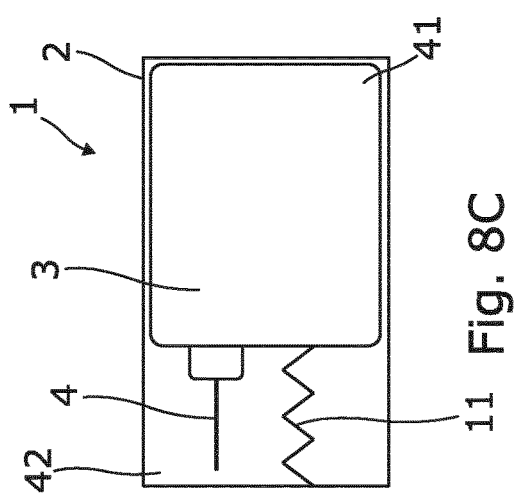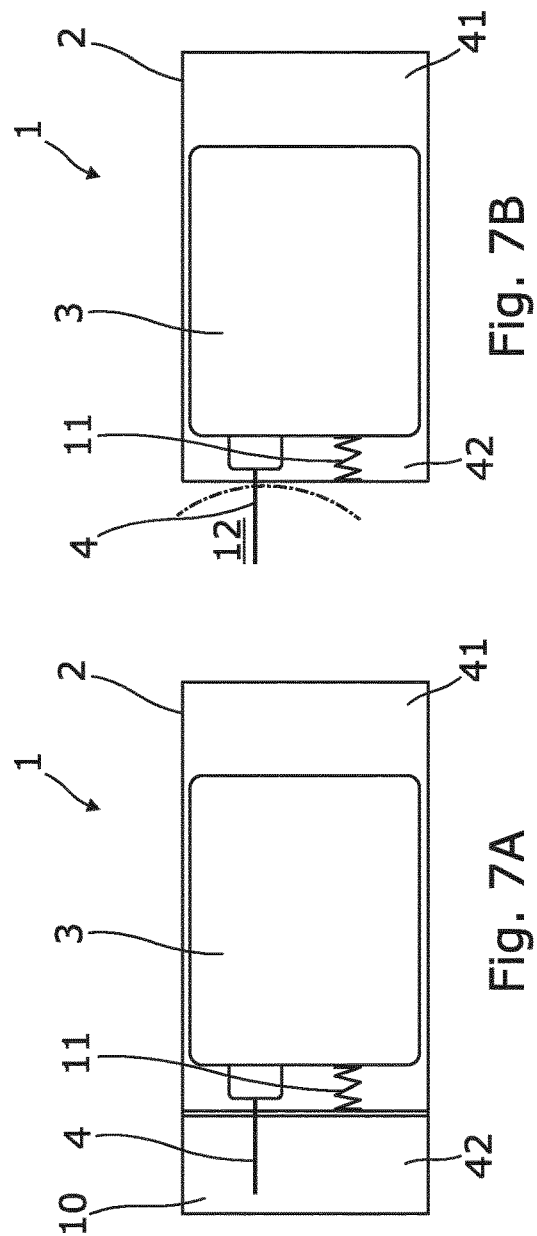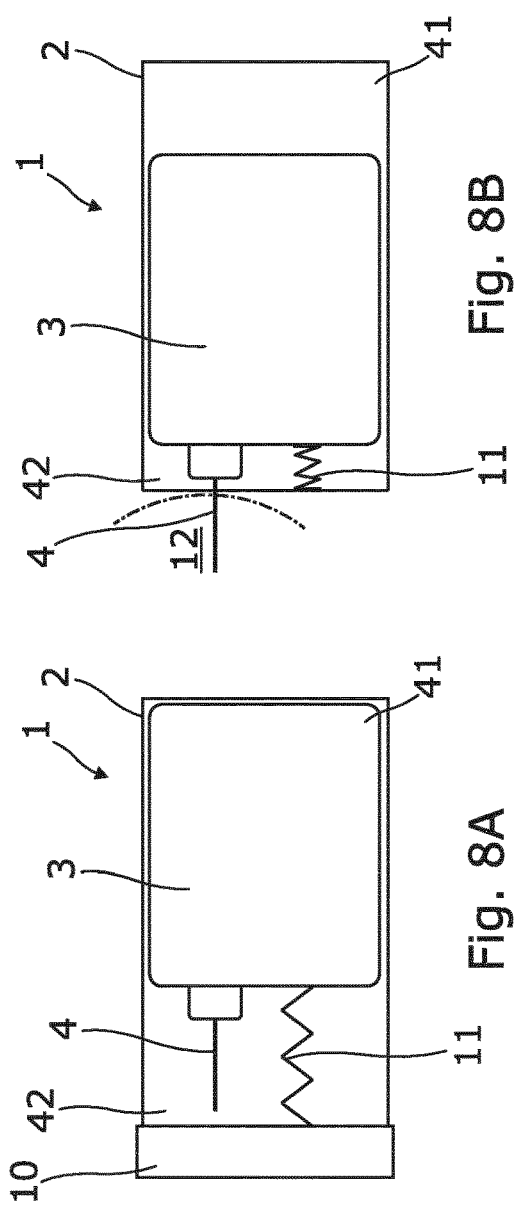

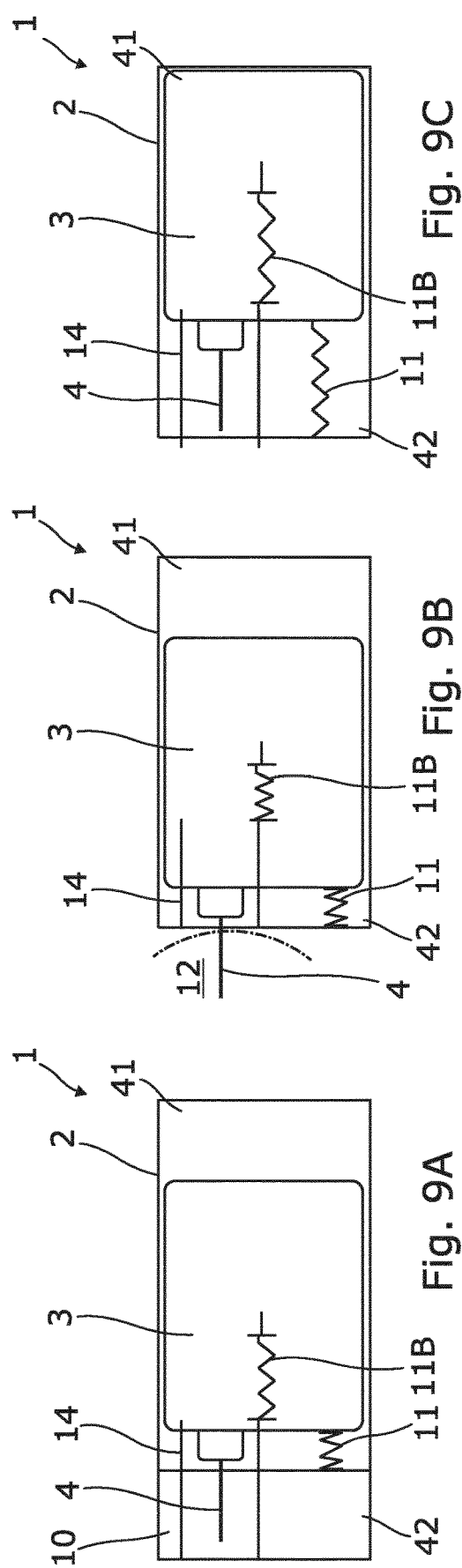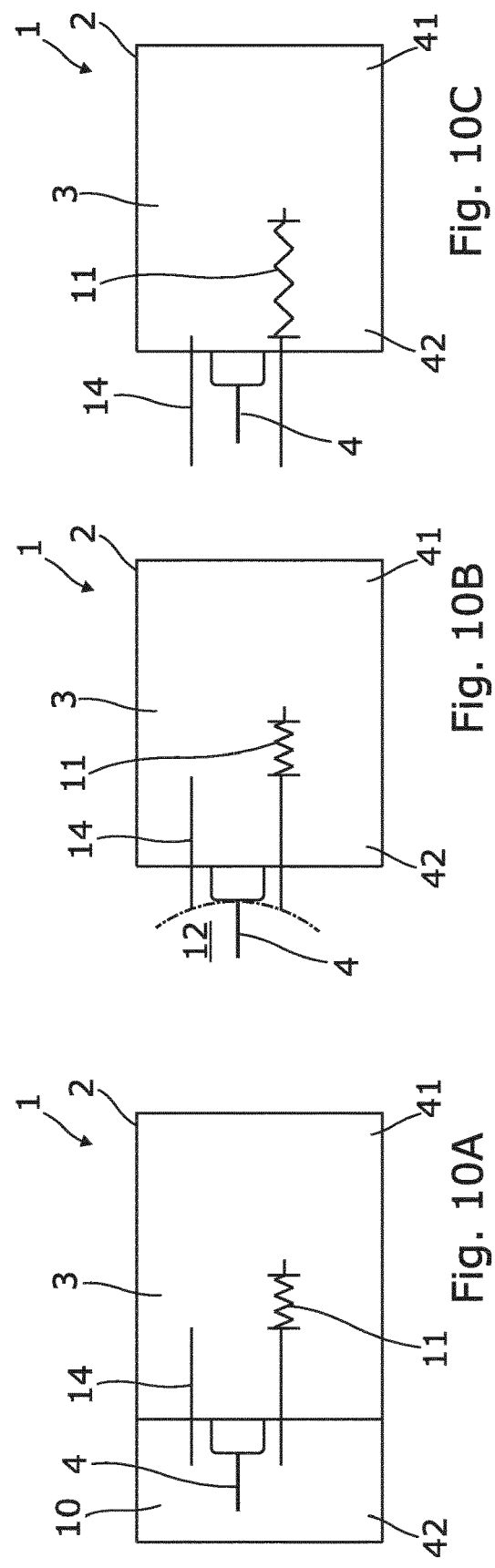

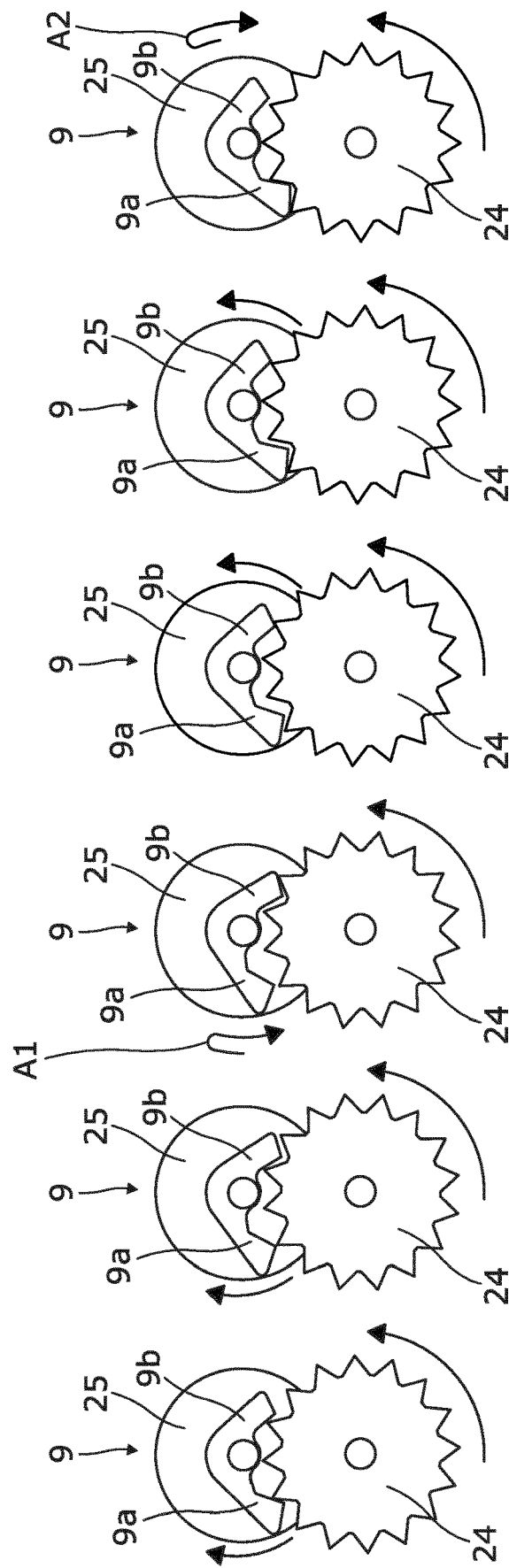

SINGLE-USE AUTO-INJECTOR

CROSS-REFERENCE TO RELATED APPLICATIONS

This is the United States national phase of International Patent Application No. PCT/EP2016/076156 filed Oct. 28, 2016, which claims the priority benefit of European Application No. 15191929.7 filed on Oct. 28, 2015. The entire contents of each of the foregoing are incorporated herein by reference.

FIELD OF THE INVENTION

The present invention relates to a single-use auto-injector for injection of a dosage of a drug into a human body.

BACKGROUND ART

It is a strong tendency that drug administration more and more often is carried out at the home of the receiver of a medicament. This implies that the administration and the handling of the equipment, e.g. an injector, must be sufficiently simple and safe to handle. When administering drugs at hospitals, it is to a higher degree possible to use highly specialised equipment comprising a larger variety of options to adjust the equipment in order to ensure correct administration.

Drugs are very expensive and some are hazardous to healthy people and some even toxic. Thus it is very important, when administering these drugs, e.g. by an injector, that the whole dose is injected into the patient, and that other persons, who are e.g. assisting the receiver in the administration of the drug, are protected from the needle after use of the injector. Furthermore, it has been found that users uncomfortable and uneasy during the injection often handle the injector or equipment in an incorrect manner. For example, the needle may be handled incorrectly and contaminated prior to use or with the disease of the receiver of the drug. Therefore, it is important that the needle is protected prior to use and safely positioned when disposing of the single-use auto-injector into a sharps container or a trash bin. With respect to home administration, the user activating and handling the auto-injector may not be the actual receiver of the drug, and hence needle protection is important in order to avoid any risk associated with handling the single-use auto-injector for such user.

Many auto-injectors of such drugs are driven by an electrical motor powered by batteries, and such auto-injectors may therefore not be environmentally correctly disposed of into a bin after injection of the drug.

SUMMARY OF THE INVENTION

It is an object of the present invention to wholly or partly overcome the above disadvantages and drawbacks of the prior art. More specifically, it is an object to provide an improved single-use auto-injector which may even be directly disposed of into a conventional trash bin.

It is a further object to provide an improved single-use auto-injector which provides needle protection after use.

It is yet another object of the present invention to provide an improved single-use auto-injector which eliminates the risk of breakage of the container/cartridge containing the medicament.

It is an object of the present invention to provide an improved single-use auto-injector which minimises noise and/or tactile movements, e.g. vibrations arising from the mechanics of the injector during use.

The above objects, together with numerous other objects, advantages and features, which will become evident from the below description, are accomplished by a solution in accordance with the present invention by a single-use auto-injector for injection of a dosage of a drug into a human body, comprising:
  a housing, and
  a dosing unit arranged in at least part of the housing, the dosing unit comprising:
    a needle,
    a drug container comprising the drug,
    a plunger movable in the container,
    a first mechanical power supply for supplying a first mechanical force for moving the plunger via a shaft to deliver a drug to the human body,
    an activation mechanism configured to release the first mechanical power of the first mechanical power supply, and
    a mechanical escapement mechanism for controlling the movement of the plunger via the shaft,
  wherein the auto-injector comprises a second mechanical power supply for supplying a second mechanical force, the auto-injector having:
    a first state in which the needle is protected from needle damage or contamination,
    a second state in which the needle is ready to penetrate the human body for dosing the drug,
    a third state in which the needle has penetrated the human body and is ready to dose, and
    a fourth state in which the needle is shielded to avoid unintended needle sticks,
  wherein the second mechanical power supply is configured to shift state of the auto-injector from the third state to the fourth state by releasing the second mechanical power.

The single-use auto-injector according to the present invention may further comprise a shield configured to shield the needle in the fourth state.

Additionally, the second mechanical power may move the shield from a retracted position in the third state to a projected position in the fourth state to protect the needle.

Moreover, the second mechanical power may move the needle into the housing from the third state to the fourth state by moving the needle and the drug container, or the whole dosing unit, into the housing.

Furthermore, the second mechanical power may be generated by retracting the shield into the housing.

Further, the second mechanical power may be generated by loading a spring.

Moreover, the second mechanical power may be a spring.

The second mechanical power may be generated by retracting the dosing unit into the housing.

Furthermore, the second mechanical power supply may be pre-loaded with the second mechanical power.

The single-use auto-injector as described above may further comprise a locking element configured to lock the auto-injector in the fourth state so as to lock the needle in its final position.

Moreover, the single-use auto-injector may further comprise a lid or a cap.

The single-use auto-injector may further comprise a needle cap.

Also, the second mechanical power supply may be a spring.

Furthermore, the activation mechanism may be configured to activate a third mechanical power of a third mechanical power supply to project the needle from the housing.

Said activation mechanism may be activated by a manual force from a user.

The single-use auto-injector as described above may further comprise a dosing lock configured to prevent unintended activation of the dosing unit.

Furthermore, the first mechanical power supply may be a spiral torsion spring. In this way it is possible to achieve that the force from the spring is transferred due to the torque from the spring. In this way it is possible to achieve an ergonomic and compact design. Furthermore, by using a spiral torsion spring, it is possible to adapt the force of the spring in a way the affects the size of the spring to a minimum.

The single-use auto-injector as described above may further comprise a mechanical transfer mechanism for controlling the transfer of power to the shaft, the mechanical transfer mechanism comprising a first gear wheel engaging the first mechanical power supply and the mechanical escapement mechanism in order to transfer power of the first mechanical power supply to the shaft. The escapement mechanism may be considered to be a mechanical brake. The escapement mechanism may also be considered to act as a viscous damper, and a viscous damper is in this relation also considered to be a mechanical brake.

Moreover, the mechanical transfer mechanism may comprise a shaft. During movement of the plunger, the shaft is connected with the piston/plunger, the shaft having teeth, and the teeth of the shaft may engage a gear wheel of the transfer mechanism. The shaft may be arranged in a position without contact with the plunger, i.e. having an air gap. In this way it is easy to install the container or cartridge. Furthermore, by having an air gap it is achieved that minor movements, e.g. during transportation, do not cause the shaft and hence the plunger to move unintentionally, which could lead to vital medicine being lost.

The auto-injector device driven by an internal force, such as a spring force, will initially i.e. before use, typically need a clearance (an air gap) between the plunger and the shaft if they are inserted individually into the device during assembling. This is due to necessary tolerances of the drug container in combination with tolerances of the various parts of the automatic injector e.g. in order to insert the container in the injector. Furthermore, an air gap between the plunger and the shaft is often present due to the fact that the plunger after filling the container with the drug, may be pushed slightly into the container in relation to the rim of the container. Hence, in order to insert the container in a direction perpendicular to the movement of the shaft a clearance, air gap is necessary.

Due to the air gap, i.e. that the shaft and the plunger initially is not in contact with each other, the lack of backpressure from the plunger will cause the shaft to accelerate towards the plunger when releasing the spring force, and hence the velocity of the shaft will increase. When the end (tip) of the shaft, reaches the plunger, the velocity and thereby the kinetic energy would be at a maximum level, and hence, so is the impulse to be transferred to the plunger at the time of impact between the plunger and the shaft. Said impulse will at least partly be transferred to the plunger. Hence, dependent of the time profile of the impact between the shaft end and the plunger, the device might experience high forces and stresses leading to deformation of components or fractures in the device or the container.

If the impact time is long and deceleration is low, the reaction forces might not be large, but if the impact time is short/instant, the deceleration is high and the reaction forces can still be large. The design of the interfaces that experience the impact affects the reaction forces. Therefore, there can be high reaction forces in several interfaces of the system, dependent of the stiffness of the component and how the energy is distributed.

It is a large and complicated task to predict the behaviour of a chain of interfaces to ensure that no part of the system will experience high forces/stresses during a high velocity/high impact. Therefore it is difficult to conclude that failure will not occur i.e. to guarantee the robustness of the system.

Instead of it being necessary to ensure the robustness of the whole auto-injector during impact, the kinetic energy and the impulse of the present invention provide controlling the mechanical mechanism after activation by controlling the velocity of the drive mechanism, i.e. the shaft.

Generally, in order to have a constant velocity in a direction, the sum of forces must be 0. It is required to have a positive force in the traveling direction in order for the system to move. If only a small increase in the velocity is needed, the acceleration and thereby the resulting force must be small.

Using an escapement mechanism as a mechanical damper/brake several advantages is achieved. A brake/damper is most often velocity-dependent, meaning that if the velocity increases, the resulting force increases. The force is determined by the damping constant for the damper and the velocity (Force=$c*v$). This is an advantage as the intention is to have the damper acting during the shaft movement in the air gap and not during dosing i.e. not necessarily during the process of forcing the drug out of the container. Hence it is achieved that only a minimum damping or braking is occurring during dosing of high viscous drugs. In this way a more powerful spring may be used without the risk of damaging the device/injector and the device may be used for a larger range of viscosities. However, if a low viscous drug is to be expelled from the container a smaller back pressure from the drug occurs. In this situation the damping using an escapement mechanism provides that the drug is administered in a slower and more gentle way. In this way the risk of damaging the drug is minimised. Furthermore, the risk of discomfort for the user during injection is minimised.

As the escapement mechanism, acting as a damper, is velocity-dependent and the velocity during dosing is relatively low, the opposite acting force from the damper is also small. Hence, it is possible to specify the escapement mechanism (damper) to provide a certain damping constant and thereby control that the velocity of the drive mechanism will reach a certain desired force equilibrium. In this way a controlled impact between the shaft and the plunger is achieved. Hence, by increasing the general robustness of the device the risk of device failure is lowered e.g. the risk of breakage of the container.

In an embodiment the shaft may be bendable.

The shaft may comprise a curved shaft or a curved piston rod. The shaft may, in its mounted position, be a curved shaft or a curved piston rod.

In addition, the force acting on the piston or shaft from the spring of the first mechanical power supply may be 1-100 N, or preferably 2-75 N, or more preferred 3-50 N, or even more preferred 4-25 N. In this way, different types of drugs having different properties, e.g. regarding viscosity, may be injected. Furthermore, the particular point in the body in which the drug is injected may cause a change in the required force.

Moreover, the housing may comprise a first carrier plate having bores through which shafts of at least the gear wheel of the mechanical transfer mechanism extend.

Additionally, the housing may comprise a second carrier plate arranged opposite the first carrier plate and at least part of the transfer mechanism may be arranged there between.

The second carrier plate may have an indentation for making room for the drug container.

Further, the gear wheel may have a shaft and may be made of metal, e.g. stainless steel.

In addition, the gear wheel may be made of plastic, or partly made of metal where the shafts of the gear wheel may be made of metal.

Also, the carrier plate may be made of plastic, such as nylon, and at least the tapering ends of the shaft may be made of metal.

By having the plates made of nylon and the shaft ends made of metal, no lubrication is required. Lubrication is not acceptable in injectors for delivering drugs as there is a risk that such lubrication will enter the human body which is unacceptable.

Furthermore, the risk of degradation of the lubricant may compromise the seize function of the injector and thereby jeopardise the health of the end-user.

The cartridge may have a volume of 0.25-50 ml. The volume of the cartridge may be larger than 10 ml. The dosage injected into the human body by the single-use auto-injector may be in the range of 0.25-10 ml, preferably in the range of 0.5-7.5 ml, more preferably in the range of 0.75-5 ml, and even more preferred in the range of 1-2.5 ml.

The needle may be projected and/or retracted in state one to four by a distance of 1 mm-75 mm, preferably 2 mm-65 mm, or more preferably 3 mm-55 mm, or even more preferred 4 mm-45 mm, or most preferred 5 mm-35 mm.

The needle may have a nominal outer diameter of approximately 0.3 mm-0.8 mm, i.e. a needle gauge of approximately 30G-21G.

Moreover, the mechanical escapement mechanism may comprise an escapement gear wheel engaging the mechanical transfer mechanism and an anchor wheel having a mass displaced from a rotation point of the anchor wheel. In this way it is possible to stop the forward movement of the piston/plunger by stopping the movement of the piston rod/shaft. The mechanical escapement mechanism may also be named as a brake, damper or an escapement brake. The escapement mechanism meters out the time of applying the force from the first mechanical force in a discrete manner. In this way it is achieved that only the desired force is released regardless of the back pressure applied to the piston rod/shaft. Hence, there is no risk of excessive force being applied to the plunger at the time of the shaft/rod getting in contact with each other, e.g. due to an air gap. If no mechanical escapement mechanism was present, a piston/shaft moving based on the potential energy from an undamped or unregulated spring force could build up kinetic energy that may cause the container/cartridge or the injector to break.

Furthermore, it is possible to control the movement of the shaft/piston rod before the shaft/piston rod is in contact with the plunger/piston. In this way it is achieved that the risk of breaking the container upon contact is eliminated. After insertion of the container/cartridge, there may be a gap, an air gap, between the contact end of the shaft and the plunger/piston. If the shaft is moved into contact with the plunger/piston with an excessive force, there is a high risk of breaking the container/cartridge, whereby a hazardous situation for the user occurs, and vital and expensive medicine is wasted.

The anchor wheel may comprise at least one second material in order to increase the mass of the anchor wheel. The second material may be metal. The second material may be fully enclosed in the anchor wheel, e.g. during a moulding process.

Finally, the dosage injected into the human body may be in the range of 0.25-10 ml, preferably in the range of 0.5-7.5 ml, more preferably in the range of 0.75-5 ml, and even more preferred in the range of 1-2.5 ml.

BRIEF DESCRIPTION OF THE DRAWINGS

The invention and its many advantages will be described in more detail below with reference to the accompanying schematic drawings, which for the purpose of illustration show some non-limiting embodiments and in which

FIG. 7A shows another single-use auto-injector in the first state in which the needle is protected from needle damage or contamination, FIG. 7B shows the single-use auto-injector of FIG. 7A in the third state in which the needle has penetrated the human body and is ready to dose, FIG. 7C shows the single-use auto-injector of FIG. 7A in the fourth state in which the dosing unit has been moved within the housing so that the needle is shielded, FIG. 8A shows yet another single-use auto-injector in the first state in which the needle is protected from needle damage or contamination by a lid, FIG. 8B shows the single-use auto-injector of FIG. 8A in the third state in which the needle is projected and penetrates the human body by moving the dosing unit in a first direction in the housing, FIG. 8C shows the single-use auto-injector of FIG. 8A in the fourth state in which the needle is retracted by moving the dosing unit in a second direction in the housing, FIG. 9A shows yet another single-use auto-injector in the first state in which a shield is projected within the lid, FIG. 9B shows the single-use auto-injector of FIG. 9A in the third state in which the shield is retracted and the needle is inserted in the body, FIG. 9C shows the single-use auto-injector of FIG. 9A in the fourth state in which the shield is projected relative to the dosing unit and the dosing unit is moved in the second direction to shield the needle, FIG. 10A shows yet another single-use auto-injector in the first state in which the shield is pre-loaded with a second mechanical power, FIG. 10B shows the single-use auto-injector of FIG. 10A in the third state in which the needle has penetrated the body and the shield is still pre-loaded with the force, FIG. 10C shows the single-use auto-injector of FIG. 10A in the fourth state in which the shield has been projected to shield the needle, FIGS. 15A-F show the sequence of movement of the escapement mechanism.

All the figures are highly schematic and not necessarily to scale, and they show only those parts which are necessary in order to elucidate the invention, other parts being omitted or merely suggested.

DETAILED DESCRIPTION OF THE INVENTION

Figure 1:
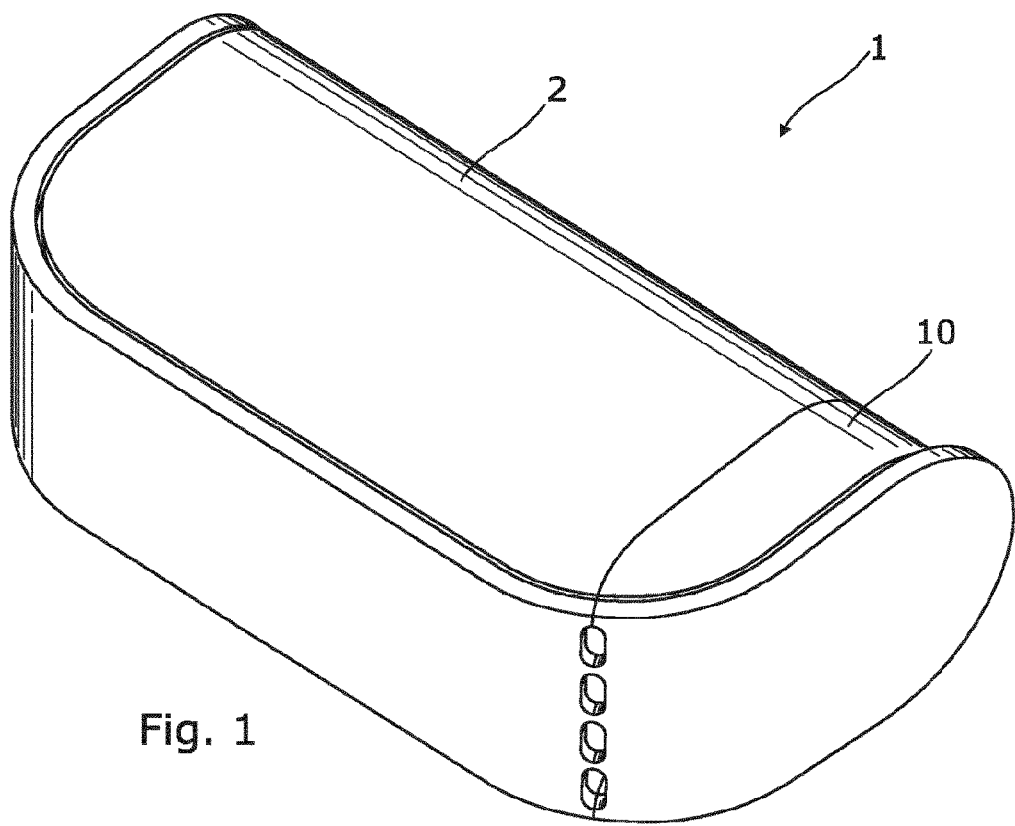
FIG. 1 shows a single-use auto-injector in perspective.
Figure 2:
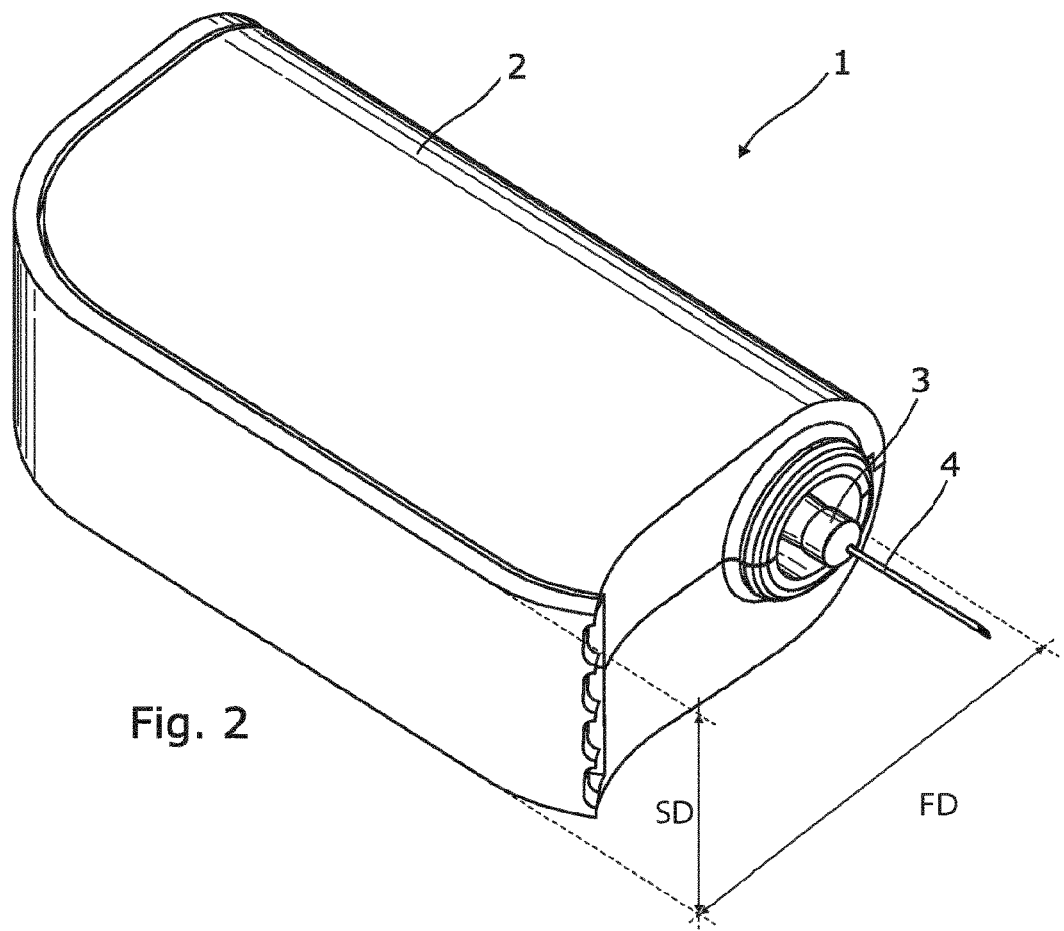
FIG. 2 shows the single-use auto-injector of FIG. 1 where the lid has been removed.

FIG. 1 shows a single-use auto-injector 1 for injection of a dosage of a drug into a human body. The single-use auto-injector 1 is shown in a first and initial stage in which the needle is protected from needle damage and/or contamination. A lid/cap 10 is shown mounted to the housing 2. In FIG. 2, the lid 10 of the single-use auto-injector has been removed and the single-use auto-injector is in a second state in which the needle is ready to penetrate the human body for dosing the drug. The single-use auto-injector 1 comprises a housing 2 and at least partly within the housing a dosing unit 3, so that a needle 4 of the dosing unit 3 projects from the housing. It is seen that the housing 2 of the single-use auto-injector 1 may have a generally square cross-section comprising housing corners having a radius. A part of the outer surface of the single-use auto-injector may have a semi-circular outline, e.g. for achieving a better ergonomic positioning in the hand of the user. The housing may have a size where the ratio of a first dimension FD in relation to a second dimension SD measured in a cross-sectional plane is more than 2:1. The dimensions are measured in the same cross-sectional plane, the plane being perpendicular to the longitudinal axis of the single-use auto-injector.

Figure 3:
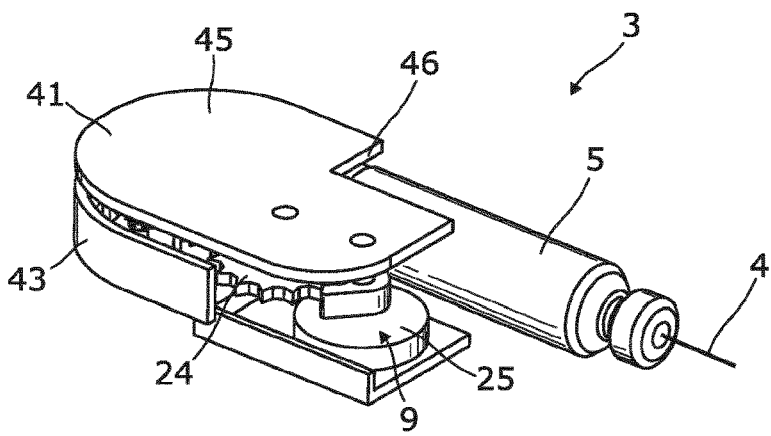
FIG. 3 shows a perspective view of a dosing unit of the single-use auto-injector.

The dosing unit 3 shown in FIG. 3 comprises a needle 4 and a drug container 5 comprising the drug. The drug container 5 may be a staked-needle, a syringe or a cartridge with a needle mounted thereto. The dosing unit 3 further comprises a first end 41. The dosing unit 3 further comprises a first carrier plate 43 and a second carrier plate 45.

Figure 4:
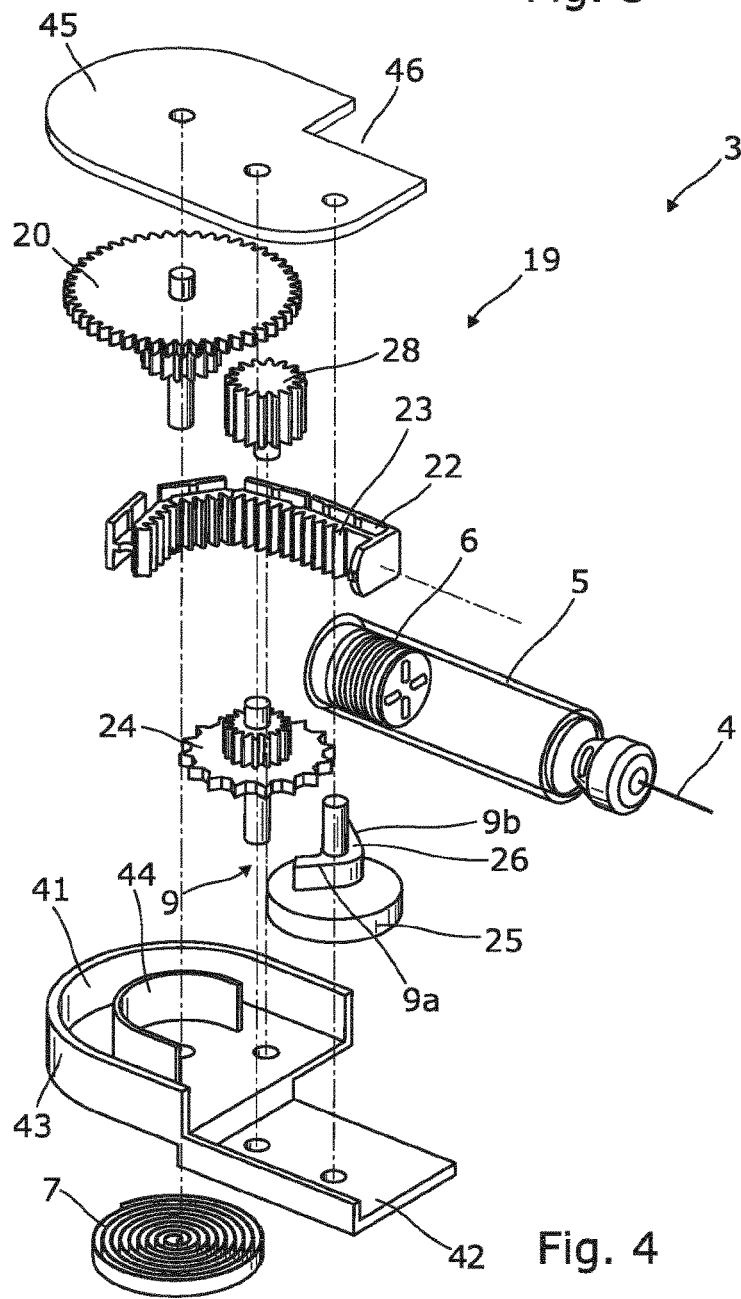
FIG. 4 shows an exploded view of the dosing unit of FIG. 3.

In the exploded view of the dosing unit 3 shown in FIG. 4 (and FIG. 4a), a piston 6 is movably arranged in the drug container 5. Via a bendable shaft 22, the piston 6 (a plunger) forces the drug out of the container 5. The force is applied from a first mechanical power supply 7, in the form of a spiral torsion spring, hence supplying a first mechanical force for moving the piston to deliver a drug to the body (not shown). It is seen that the spiral torsion spring 7 acts in a manner so that the torque delivered from the spiral spring is transferred to the first gear wheel 20. The dosing unit 3 further comprises an activation mechanism 8 (shown in FIG. 5A) configured to release the first mechanical power of the mechanical power supply 7. The dosing unit 3 comprises a mechanical escapement mechanism 9 for controlling the movement of the piston 6 by controlling the speed of rotation of the mechanical power supply, i.e. the delivery of force from the spiral torsion spring 7. The escapement mechanism 9 comprises an anchor wheel 25 having a mass. The escapement gear wheel 24 interacts with arms of the anchor wheel 25 and the change in direction of rotation of the anchor wheel 25 creates a braking of the movement of the shaft 22. In this way, it is achieved that a significant, excessive force of the spring 7 can be controlled in a simple manner, and thereby it is possible to administer drugs of highly different viscosities over the same time span. This even implies drugs of high viscosities that demand a high force applied to the plunger.

Figure 4A:
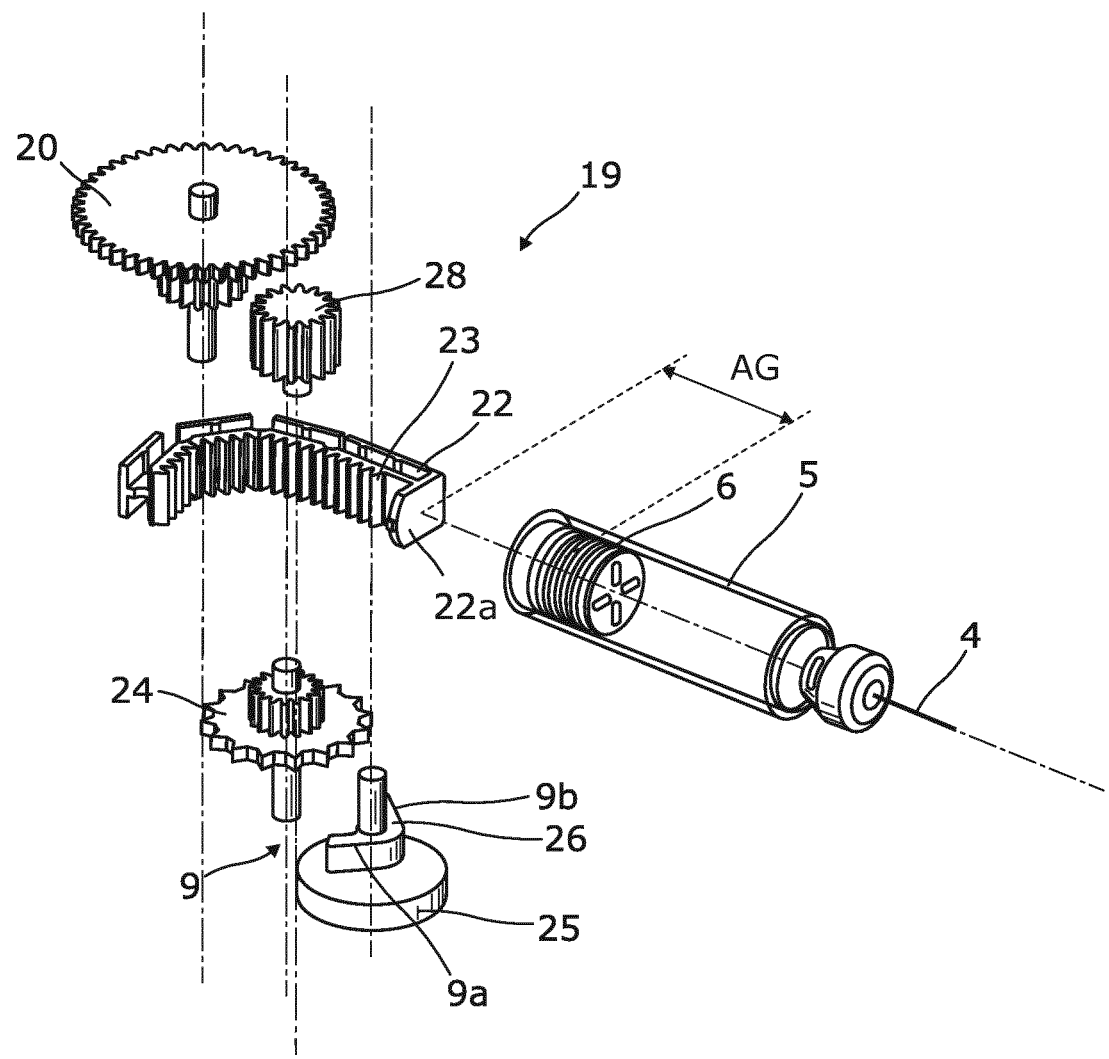
FIG. 4A shows an enlarged view of an air gap between a plunger and a shaft/piston.

Referring again to FIG. 4 and partly to FIG. 4a, the dosing unit 3 further comprises a mechanical transfer mechanism 19 for controlling the transfer of power to the piston 6. The mechanical transfer mechanism 19 comprises a first gear wheel 20 engaging the first mechanical power supply 7 and the mechanical escapement mechanism 9 in order to transfer power of the first mechanical power supply 7 to the piston 6. The mechanical transfer mechanism 19 comprises a shaft 22 connected to the piston/plunger 6, the shaft having teeth 23, which engage the gear wheel 28 of the transfer mechanism 19. The shaft 22 is bendable so as to be able to slide along the rounded corners of the generally square-shaped housing 2. In this way, it is achieved that the overall size of the single-use auto-injector 1 may be reduced. The shaft 22 is arranged in a first end 41 of the single-use auto-injector 1 and the needle 4 is arranged in a second end 42 opposite the first end. As shown in FIG. 4, the single-use auto-injector has a first carrier plate 43 which forms a basis plate having a guiding part 44 for guiding the shaft while moving. The single-use auto-injector 1 further comprises a second carrier plate 45 which forms a cover part of the dosing unit 3, as shown in FIG. 3. The second carrier plate 45 has an indentation 46 so as to provide room for the drug container 5.

The mechanical escapement mechanism 9 comprises an escapement gear wheel 24 engaging the mechanical transfer mechanism 19 and an anchor wheel 25 having an anchor mechanism 26 comprising anchors 9a, 9b (shown in detail in FIG. 15). In this way, as the first mechanical power supply 7 forces the first gear wheel 20 of the mechanical transfer mechanism 19 to rotate and thus move the shaft and the piston, the gear wheel 24 engages the first gear wheel 20. The escapement gear wheel 24 engages the anchor mechanism 26. As the gear wheel 24 rotates, the anchors 9a, 9b of the anchor mechanism 26 will engage and disengage, such that anchor 9b will engage with gear wheel 24, just as anchor 9a has disengaged from gear wheel 24, and vice versa. This will cause the direction of rotation of the anchor wheel 25 to change every time the engagement with the gear wheel 24 switches between the two anchors 9a, 9b. Since the anchor wheel 25 has a mass being accelerated and decelerated every time the direction of rotation of the anchor wheel 25 is reversed, this will cause the rotational speed of the gear wheel 24 to be limited, hence causing the speed of the shaft 22 to be limited, which in turn causes the speed of the shaft and thereby the plunger 6 to be controlled.

FIG. 4A shows an enlarged view of the air gap AG between the plunger and the first end 22a of the shaft/piston rod 22. When an air gap AG is present, it is seen that initial movement of the shaft 22 will have no back pressure from the plunger/piston 6. Hence, if no mechanical escapement mechanism (situation not shown) is present and the full potential energy of the spring is released too fast, the shaft 22 potentially causes the container or cartridge 5 to break because it will cause sudden shock to the container 5 on impact of the first shaft end 22a and the plunger 6.

Every time potential energy from the torsional spiral spring 7 is released (see FIG. 4) the mechanical escapement mechanism 9 ensures that the same amount of energy is released as long as sufficient force is available in the spring. In this way it is possible to control that the force is sufficient to move the plunger 6 the whole way in the container, i.e. that sufficient spring force is applied from the shaft to the plunger, but also that the resulting force applied is safely below the level that would cause the container 5 to break upon the initial impact between the shaft and the plunger. Reference numerals shown but not discussed under FIG. 4a is shown in order to relate FIG. 4a to FIG. 4.

FIGS. 5A-E show that the single-use auto-injector 1 further comprises a second mechanical power supply 11 shown for supplying a second mechanical force. The second mechanical power supply 11 is configured to keep the shield 14 projected unless a force excessive to the force of the second mechanical power supply is applied to the shield in the longitudinal direction, i.e. parallel to the needle. Such excessive force could be applied by the user by forcing the shield 14 towards the skin/body 12 of a human. The second mechanical power supply 11 shifts state of the single-use auto-injector 1 from a third state in which the needle has penetrated the human body 12, illustrated by a dotted line (FIG. 5C), and is ready to dose to a fourth state in which the needle is shielded to prevent unintended needle sticks. The shift of state from the third state to the fourth state is performed by releasing the second mechanical power/force from the second mechanical power supply 11.

Figure 5A:
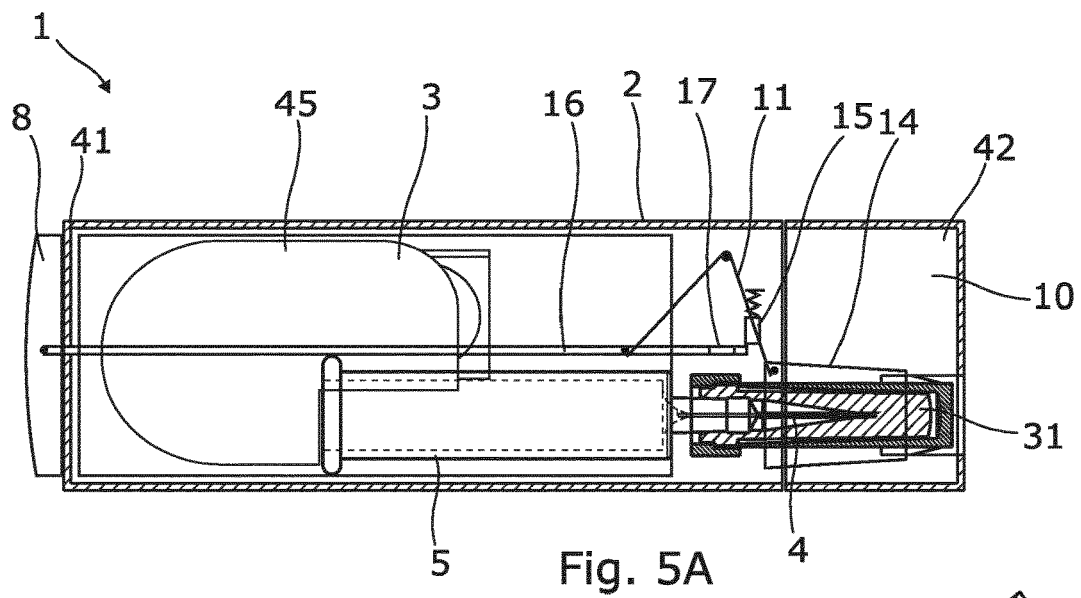
FIG. 5A shows a single-use auto-injector in a first state in which the needle is protected from needle damage or contamination.

The single-use auto-injector 1 is in FIG. 5A shown in its first state and in the initial position in which the needle 4 is hidden and protected from needle damage or contamination. The lid or cap 10 is attached to the housing 2. The lid 10 is shown comprising additional protection of the needle 4. The additional protection of the needle extends inside the shield 14.

Figure 5B:
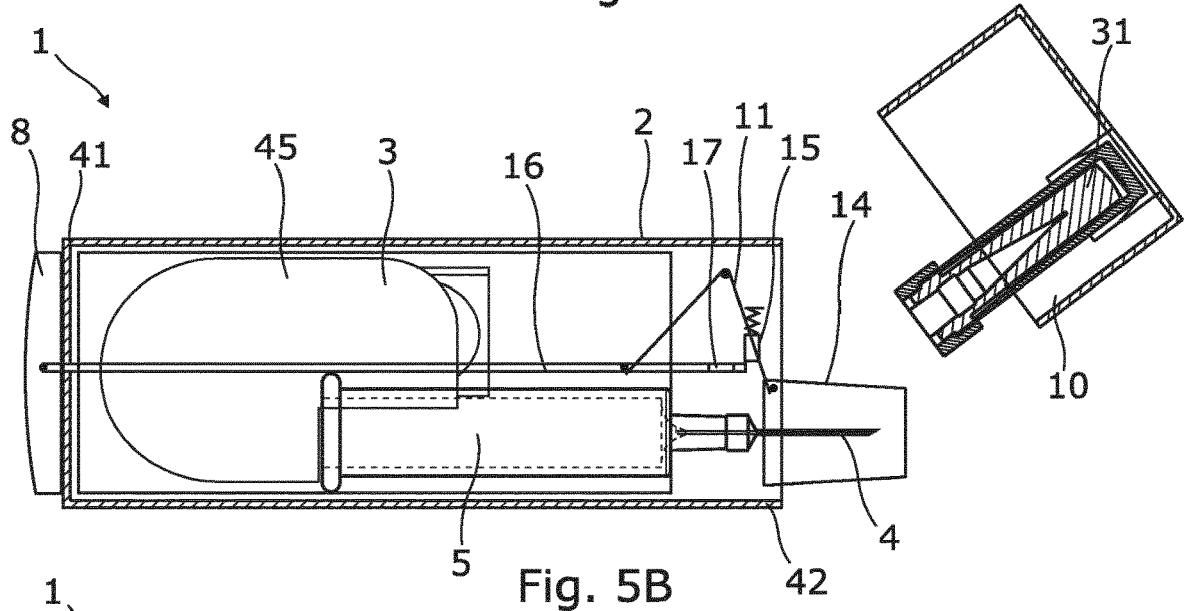
FIG. 5B shows the single-use auto-injector of FIG. 5A in a second state in which the needle is hidden by a shield and is ready to penetrate the human body for dosing the drug.

FIG. 5B shows the single-use auto-injector 1 in its second state. The cap/lid 10 is removed and the needle 4 is ready to penetrate the human body for dosing the drug, such as a medicament for curing or easing the pain of a patient.

Figure 5C:
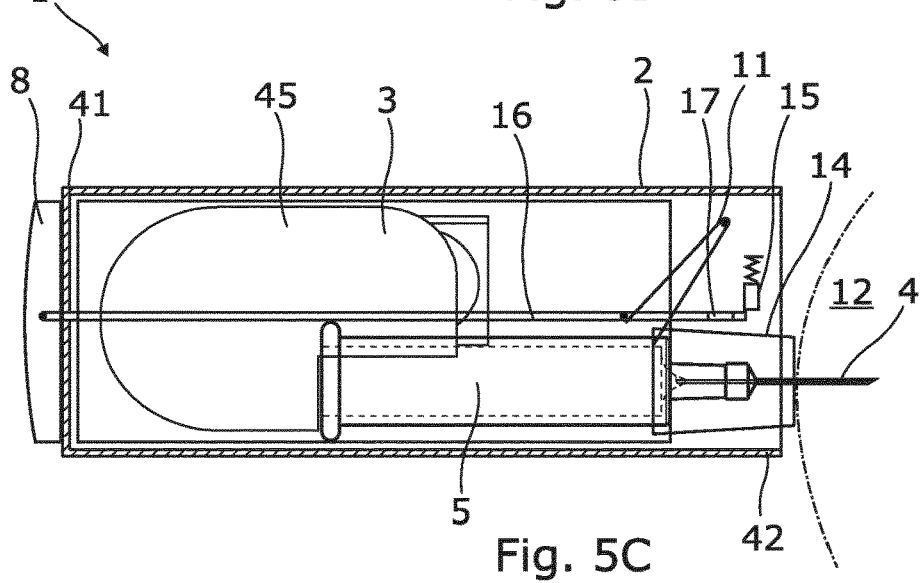
FIG. 5C shows the single-use auto-injector of FIG. 5A in a third state in which the needle has penetrated the human body and is ready to dose.

In FIG. 5C, the single-use auto-injector 1 is shown in its third state in which the needle 4 has penetrated the human body 12, (the skin of the body illustrated by a dotted line), and the single-use auto-injector 1 is ready to dose the drug into the human body 12, e.g. in the cutaneous layer. It is shown that the shield 14 is forced into the housing 2 when inserting the needle 4 into the body. When forcing the shield 14 into the housing 2, the spring 11 i.e. the second mechanical power supply is tensioned and ready to push the shield back to its position in state two (shown in FIG. 5B).

Figure 5D:
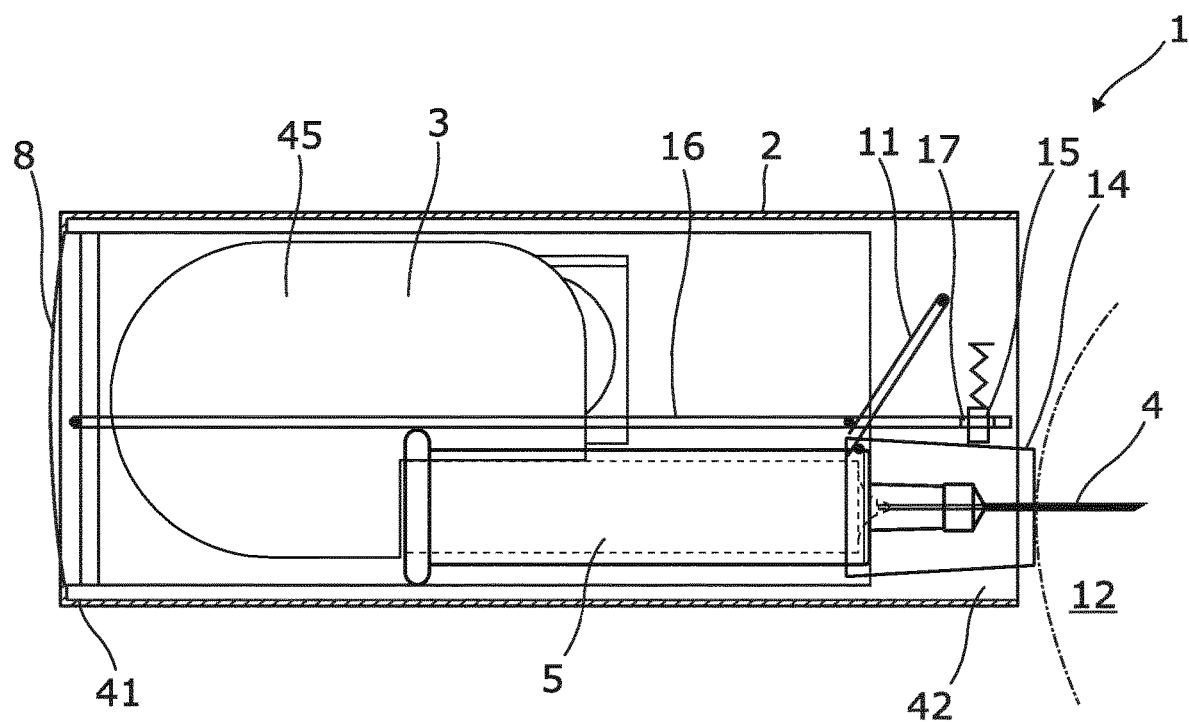
FIG. 5D shows the single-use auto-injector of FIG. 5A in an intermediate state between the third state and the fourth state.

FIG. 5D shows an intermediate state of the single-use auto-injector 1 in which a locking element 15 is activated. The locking element 15 is activated when pressing the button 8 which also initiates the injection of the drug. The intermediate state of FIG. 5D occurs when moving the single-use auto-injector 1 from the third state to the fourth state.

Figure 5E:
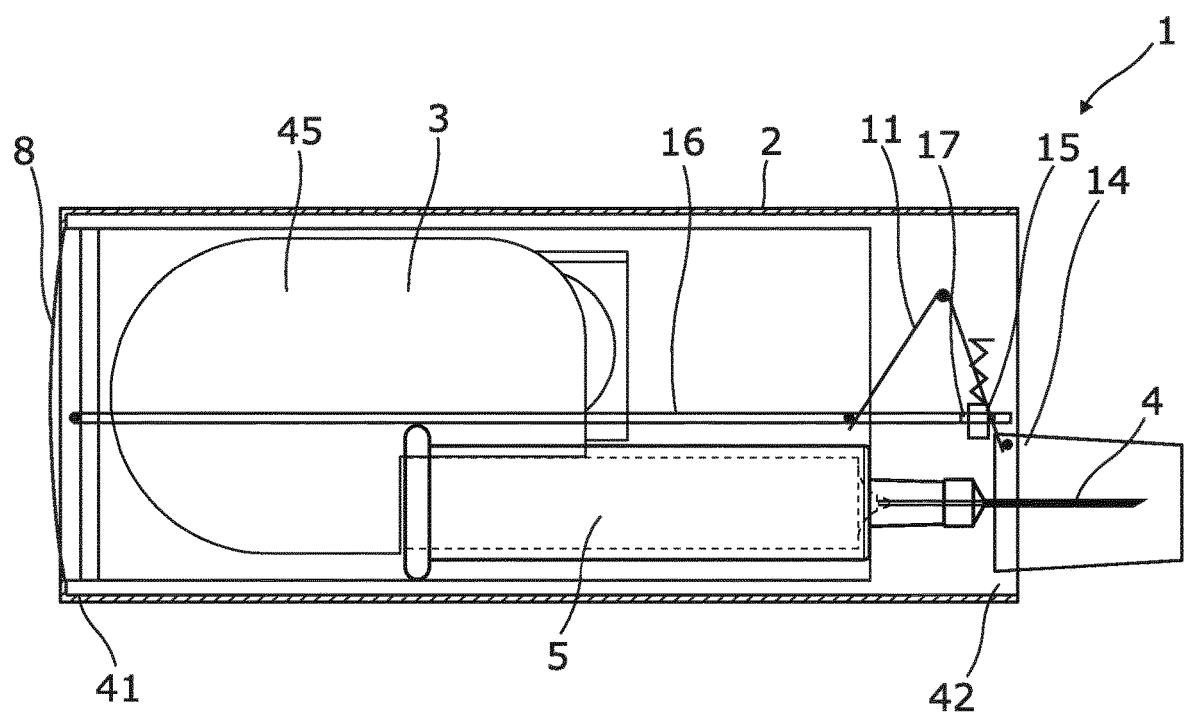
FIG. 5E shows the single-use auto-injector of FIG. 5A in a fourth state in which the needle is shielded to avoid unintended needle sticks.

The single-use auto-injector 1 is in FIG. 5E shown in its fourth state in which the needle is shielded to avoid unintended needle sticks. Hence the single-use auto-injector 1 can be handled safely and may even be thrown into a conventional trash bin in the home of the user. The single-use auto-injector 1 is thus fully mechanically operated and requires no batteries or electrical wiring. Hence, the single-use auto-injector 1 of the present invention is to be environmentally correctly disposed of into a conventional bin. Furthermore, the single-use auto-injector 1 can easily be stored in the refrigerator which is often the best storing place for an auto-injector having a pre-inserted drug. However, storing in a refrigerator is often not good for the electrical components present in known injectors and hence storing of the drug in the injector is often not possible. These injectors therefore have to be fitted with batteries or otherwise prepared before use, which induces a risk that the user is not capable of doing so, and thus induces a risk of failure in such known injectors.

In FIGS. 5A-E, the single-use auto-injector 1 comprises a shield 14 configured to shield the needle in the fourth state. As can be seen, the needle 4 in FIGS. 5A-E is also protected in the second state before it is injected into the human body 12, and thus the needle 4 is also shielded and hence hidden from the user. This is especially useful to people suffering from aichmophobia (fear of needles). As shown in FIGS. 5B-C, the second mechanical power of the second mechanical power supply 11 is generated when the needle 4 penetrates the human body 12 as the shield 14 moves from a projected position in the second state to a retracted position in the third state. When forcing the shield 14 into the housing 2, the second mechanical power supply 11, being a spring, is stretched or tensioned, thus generating the second mechanical power. As shown in FIGS. 5C and 5E, the second mechanical power of the second mechanical power supply 11 moves the shield 14 from a retracted position in the third state to a projected position in the fourth state to protect the needle 4.

The single-use auto-injector 1 of FIGS. 5A-E further comprises a locking element 15 configured to maintain the single-use auto-injector 1 in the fourth state. This is carried out by locking the shield 14 in the projected position in which it surrounds and shields the needle 4. The single-use auto-injector 1 further comprises a dosing lock 16 configured to prevent unintended activation of the dosing unit before the needle 4 is safely injected into the human body 12 and the user is ready to receive the drug. The dosing lock 16 has an opening 17 which in the inactivated state of the single-use auto-injector 1 is unaligned with the locking element 15, and when in the activated state the opening 17 is aligned with the locking element 15 so that the locking element 15 extends into the opening as shown in the intermediate position shown in FIG. 5D. After injection of the drug is completed, the shield 14 projects from the housing 2 and the projected shield has surpassed the locking element 15. Hence, the locking element 15 is allowed to project further through the opening 17 and be positioned behind the shield 14, so that the shield cannot be pushed back into the housing 2. As can be seen in FIG. 5A, the single-use auto-injector 1 further comprises a needle cap 31, which is arranged as part of the lid 10. The dosing lock 16 is in contact with the activation mechanism 8, e.g. a button in the one end part of the single-use auto-injector, and the button cannot be pressed when the lid 10 is still mounted on the single-use auto-injector 1.

Figure 6A:
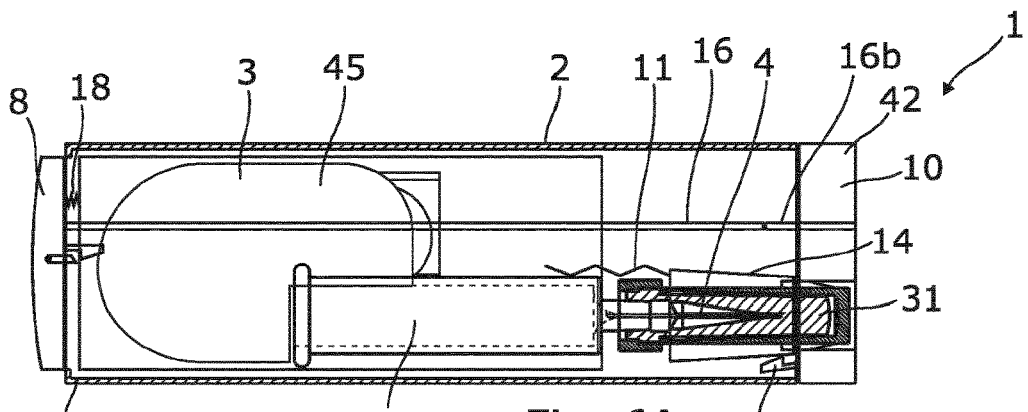
FIG. 6A shows another single-use auto-injector in the first state in which a third mechanical power supply is used to project the needle from the housing.
Figure 6B:
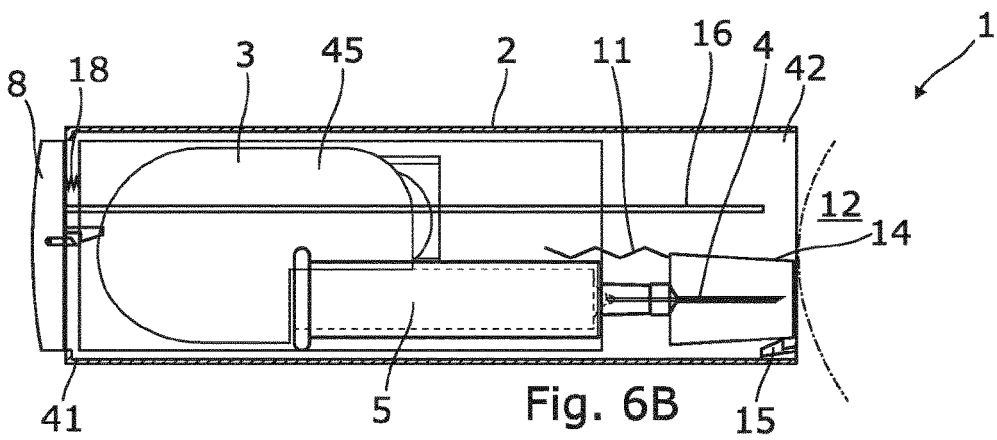
FIG. 6B shows the single-use auto-injector of FIG. 6A in the second state in which the lid has been removed.
Figure 6C:
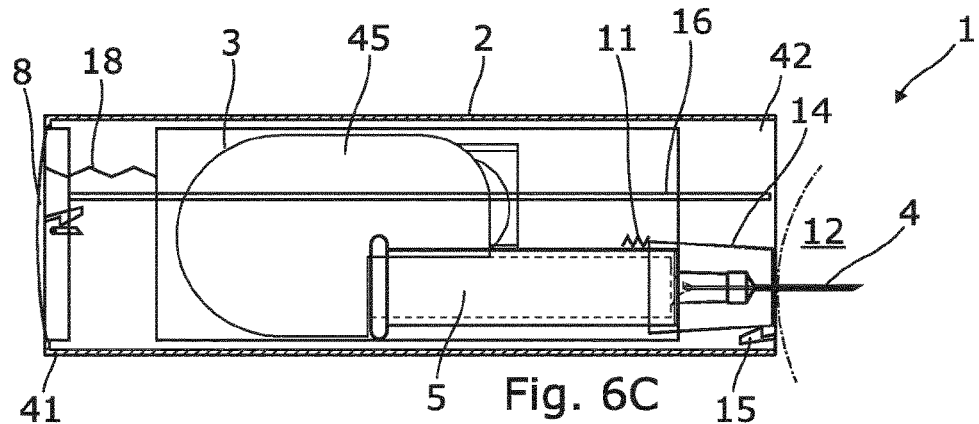
FIG. 6C shows the single-use auto-injector of FIG. 6A in the third state in which the needle has penetrated the human body and is ready to dose.
Figure 6D:
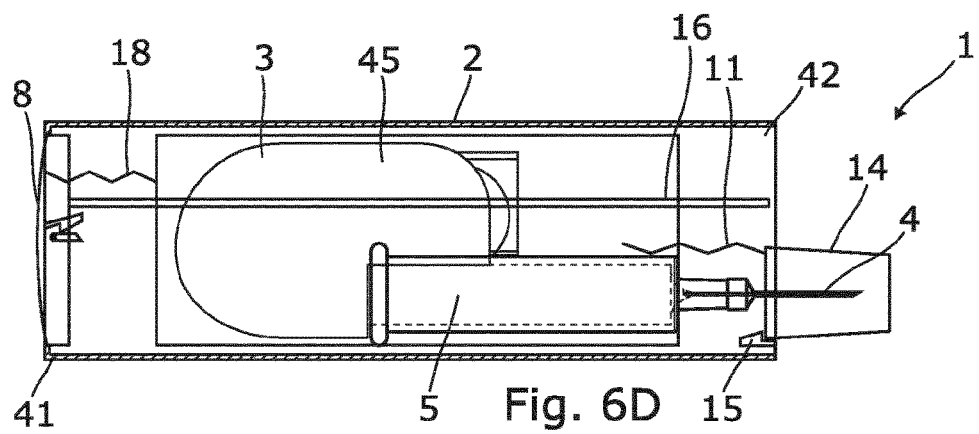
FIG. 6D shows the single-use auto-injector of FIG. 6A in the fourth state in which the needle is shielded to avoid unintended needle sticks.

As shown in FIGS. 6A-D, the activation mechanism 8 is configured to activate a third mechanical power of a third mechanical power supply 18 to project the needle 4 from the housing 2. In FIG. 6A, the activation mechanism 8 is prevented from projecting the needle from the housing by a safety part 16b in the lid 10. The user arms the single-use auto-injector by removing the cap 10. FIG. 6B shows that the cap 10 is removed but the needle 4 is still not visible for the user as it is still retracted into the housing 2. In FIG. 6C, the activation mechanism 8 has been activated by a manual force from the user. When activating the auto-injector, the third mechanical power supply 18 forces the dosing unit 3 and thereby the needle 4 out of the housing 2, and the needle penetrates the human body 12. As the single-use auto-injector 1 moves from second state shown in FIG. 6B to the third state shown in FIG. 6C, the second mechanical power supply 11 comprising a spring is loaded or tensioned with the second mechanical power by compressing the spring 11 i.e. the second mechanical power supply. The shield 14 is still kept in a retracted position in the housing 2 due to the one end part of the shield 14 being in contact with the skin of the user. When the user withdraws the single-use auto-injector 1 and thus withdraws the needle 4 out of the human body 12, the second mechanical power supply 11 forces the shield 14 to automatically project out of the housing 2 and thereby shield the needle 4. The locking element 15 ensures that the shield 14 is kept and locked in a projected position and hence kept in a position shielding the user and people handling the single-use auto-injector from the needle 4.

In FIGS. 7A-C, the single-use auto-injector 1 is pre-loaded with the second mechanical power of the second mechanical power supply 11 and after end of dosing, the second mechanical power moves the needle 4 into the housing 2, i.e. from the third state to the fourth state by moving the needle 4, the drug container 5 and the whole dosing unit 3, into the housing 2 towards the first end 41. In this embodiment, the second mechanical power may be generated by loading a spring when manufacturing the single-use auto-injector 1.

As shown in FIGS. 8A-C, the second mechanical power is generated by retracting the dosing unit 3 into the housing 2 when penetrating the needle 4 into the human body 12. Forcing the dosing unit 3 and the needle 4 out of the housing may be done by the user. Thus, the dosing unit 3 is moved from the position in FIG. 8A towards the state/position in FIG. 8B, e.g. by the user, and the dosing unit is thus moved from the first end 41 towards the second end 42 in a first direction. Subsequently, after finished injection the dosing unit 3 and the needle 4 are moved to the position shown in FIG. 8C by moving the dosing unit 3 in a second direction opposite the first direction and thus towards the first end 41. In this position of the dosing unit 3 and hence the position of the needle 4, the needle is safely retracted into the housing and the housing serves as a shield for needle stick prevention. Depending on the level of safety, the lid 10 may be a membrane, e.g. comprising an impenetrable area to be removed before projection of the needle is possible.

As can be seen from FIGS. 9A-C, the single-use auto-injector 1 is pre-loaded with the second mechanical power of the second mechanical power supply 11. FIG. 9A shows that the lid 10 is still mounted on the housing 2. After the lid 10 has been removed, the shield 14 is still projecting from the housing 2 and hence protecting the needle 4. When pressing the shield 14 towards the skin 12 of the user, the shield is forced into the housing 2, and hence the needle 4 is capable of penetrating the skin of the user. After end of dosing, the user removes the single-use auto-injector 1, and as the user removes the injector, the shield 14 will stay in contact with the skin, and therefore the needle 4 is fully shielded at all times. The shield 14 is kept in contact with the skin 12 by an additional second mechanical power 11B moving the shield 14 to project from the dosing unit 3 and surrounding the needle 4. Furthermore, after end of dosing and when the shield 14 is no longer in contact with the skin, the second mechanical power 11 moves the dosing unit 3 further into the housing 2 towards the first end 41 of the housing. As the needle penetrates the human body 12, the additional second mechanical power is generated by compressing the spring 11B.

In FIGS. 10A-C, the second mechanical power supply 11 is pre-loaded with the second mechanical power, e.g. a spring. At end of dosing, the second mechanical power supply 11 is activated and the shield 14 is projected to shield the needle 4.

Figure 11:
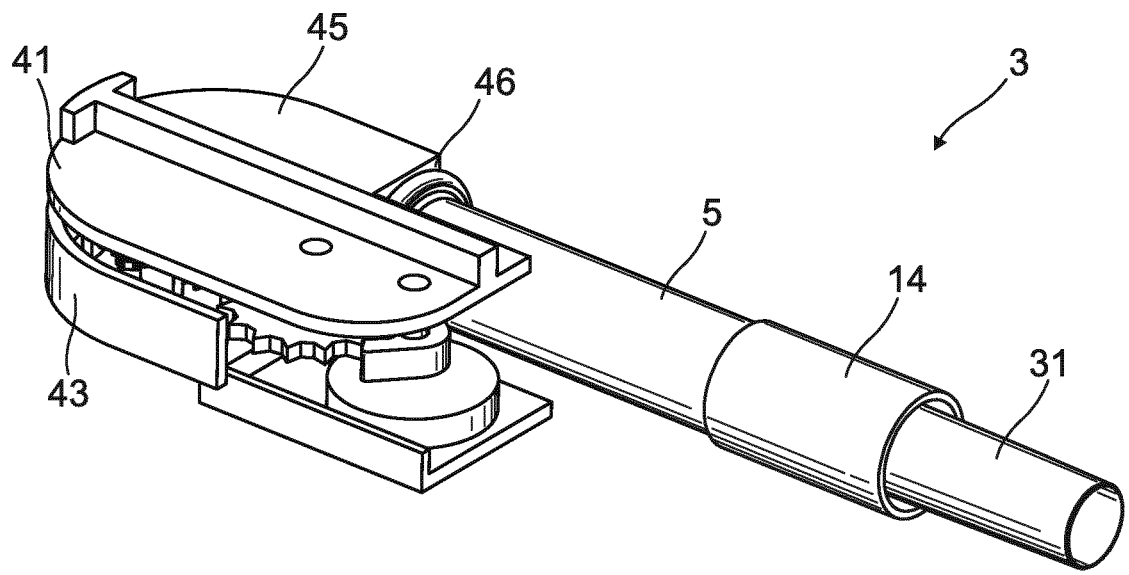
FIG. 11 shows a perspective view of another dosing unit comprising a needle shield.
Figure 12:
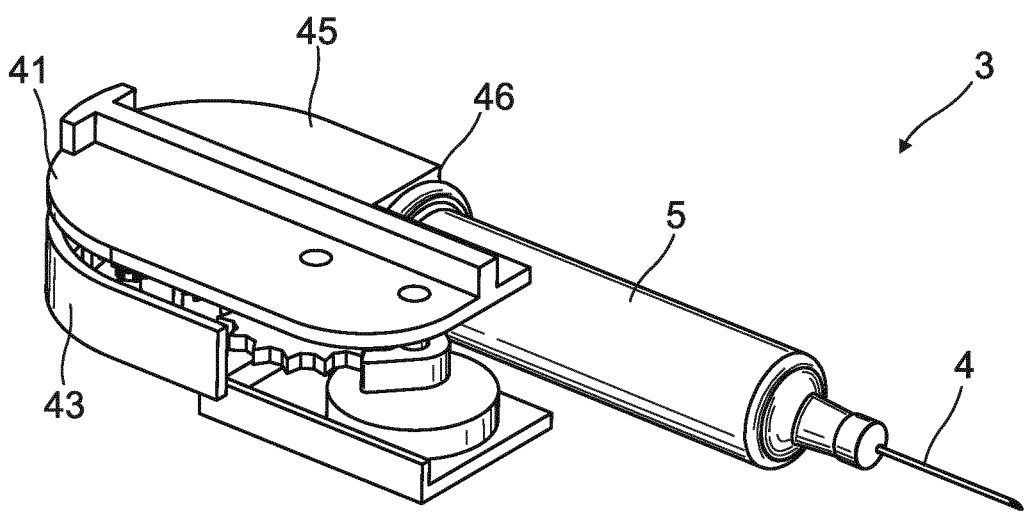
FIG. 12 shows the dosing unit of FIG. 11 where the shield has been removed.
Figure 13:
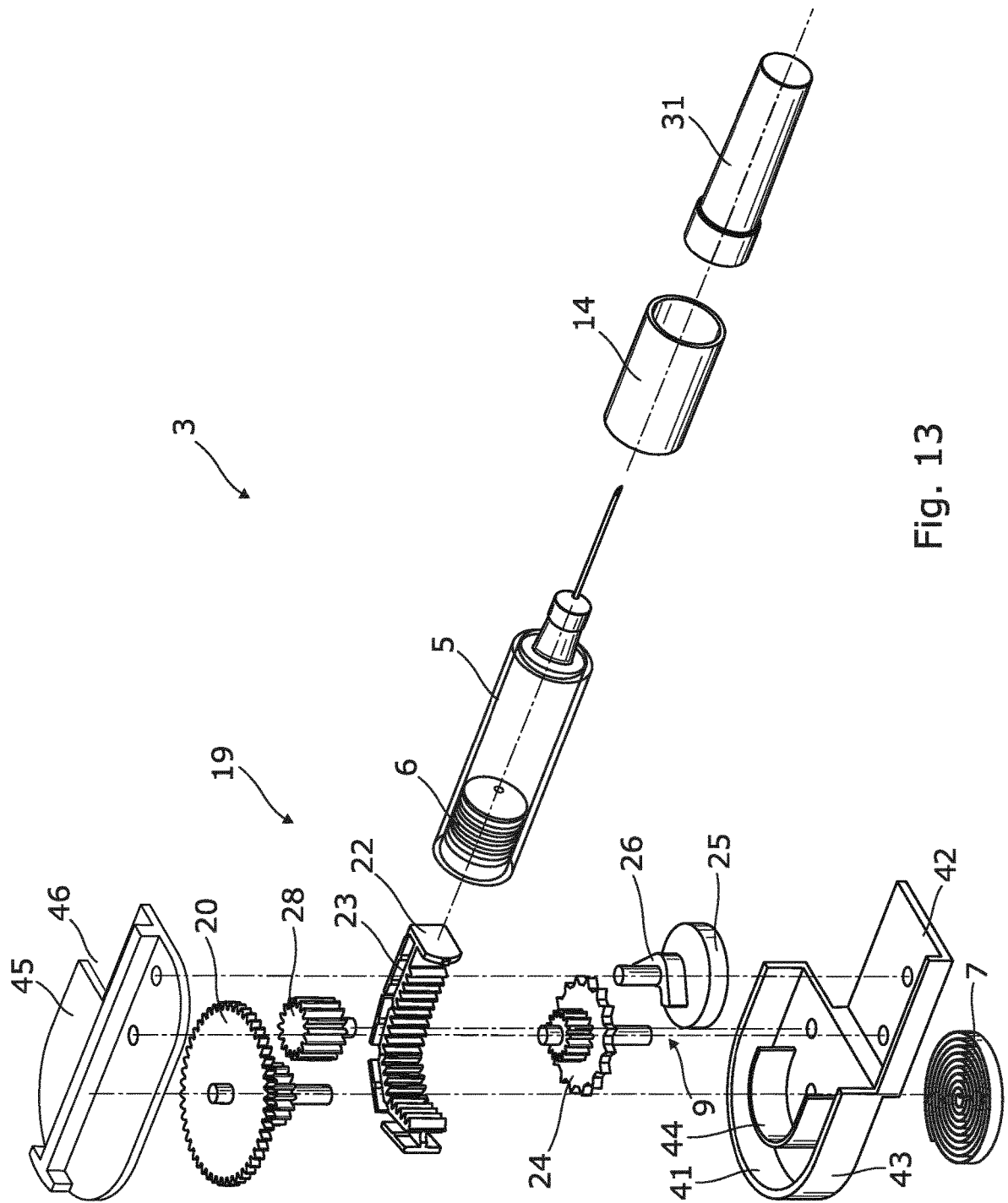
FIG. 13 shows an exploded view of the dosing unit of FIG. 11, FIGS. 14A-D show the single-use auto-injector of FIG. 11 in the four states.

In FIG. 11, the dosing unit 3 is shown in perspective having a needle cap 31 covering the needle 4 (needle 4 is shown in FIG. 12). In the exploded view in FIG. 13, the dosing unit 3 has substantially the same elements and design as the dosing unit of FIG. 4, but in FIG. 13, the dosing unit 3 further comprises the shield 14 and a needle cap 31. It is seen that the needle 4 is fixedly mounted on the container 5, e.g. as a stack needle or a syringe. It will be understood by the person skilled in the art that different containers may be used, e.g. a cartridge (as shown in FIG. 4).

Figure 14A:
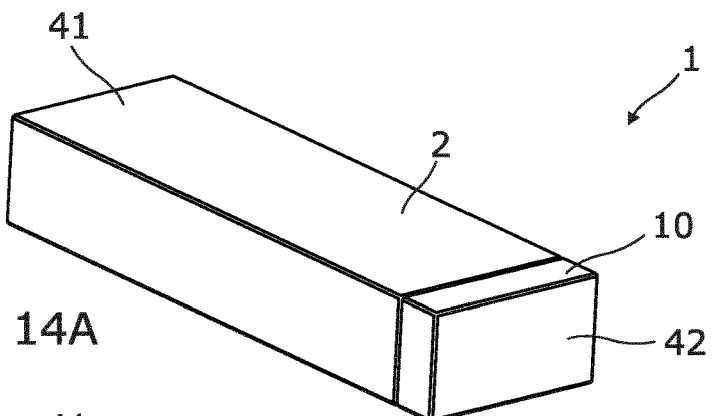
Figure 14B:
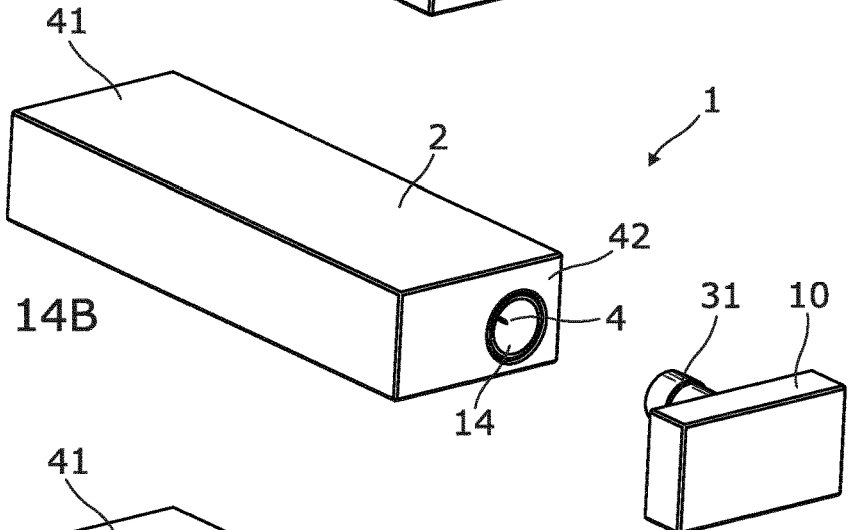
Figure 14C:
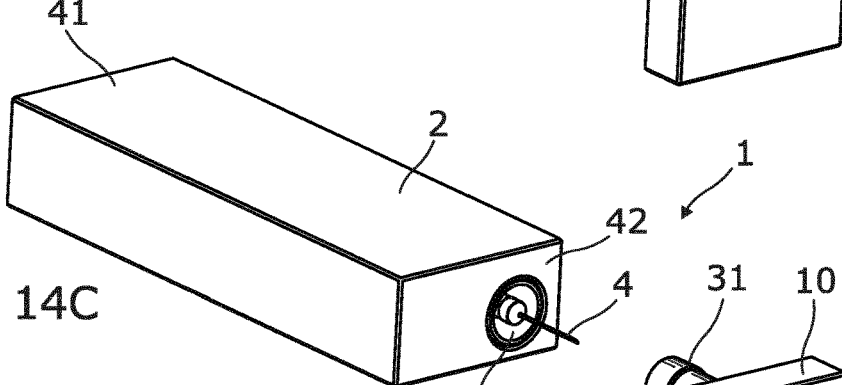
Figure 14D:
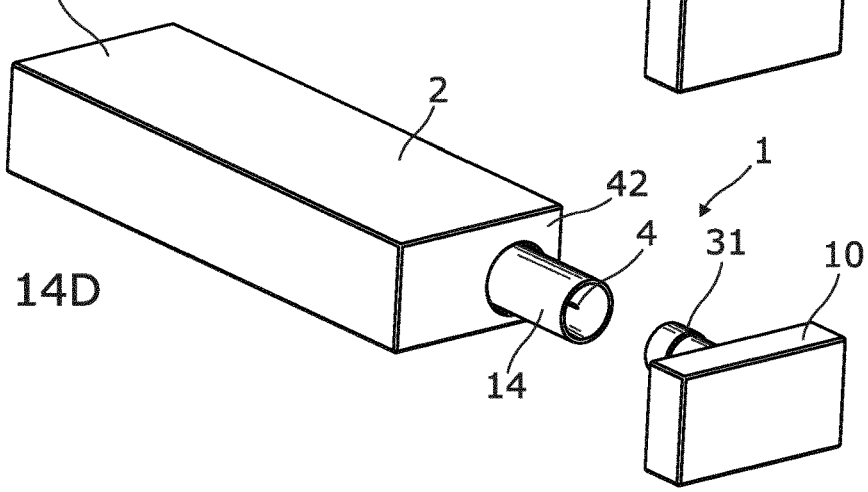

The single-use auto-injector 1, shown in FIGS. 14A-D, has a more square cross-sectional shape than the single-use auto-injector 1 shown in FIGS. 1 and 2. The single-use auto-injector 1 of FIG. 14A is shown in its first state, i.e. with a lid or a cap mounted, and in its second state in FIG. 14B. In FIG. 14C, the needle 4 of the single-use auto-injector 1 is in its projected position and the needle has penetrated the human body (not shown). In FIG. 14D, the single-use auto-injector 1 is in its fourth and shielded state in which the shield 14 surrounds the needle 4.

FIG. 15 shows the mechanical escapement mechanism 9 and the function in detail. The braking is achieved by the escapement gear wheel 24 turning, and when turning, the escapement gear wheel 24 needs to force the mechanical escapement mechanism 9 to turn too. The anchor mechanism comprises anchors 9a, 9b attached to the anchor wheel 25. The anchors 9a, 9b of the mechanical escapement mechanism 9 engage the escapement gear wheel 24 and are arranged to cause the mass of the anchor wheel 25, i.e. the mass of the escapement mechanism 9, to shift direction of rotation. This shifting of the rotational direction of the anchor wheel 25 and hence the general mass of the escapement mechanism 9 creates a braking effect. The anchor wheel 25 shifts rotational direction in FIG. 15C and in FIG. 15F according to the arrows A1 and A2. The anchor wheel 25 turns clockwise in FIGS. 15A and 15B, and counter clockwise in FIGS. 15C, 15D and 15E and again clockwise in FIG. 15F. The escapement mechanism 9 ensures that the main source of power, i.e. the first power source, releases its power in a controlled manner. In this way, a gap between the shaft and the plunger/piston inserted in the drug container, i.e. an air-gap, does not cause an unintended sudden impact from the shaft or from the stem that could cause the container to fail or crack.

Although the invention has been described in the above in connection with preferred embodiments of the invention, it will be evident for a person skilled in the art that several modifications are conceivable without departing from the invention as defined by the following claims.

The invention claimed is:

1. A single-use auto-injector for injection of a dosage of a drug into a human body, comprising:
    a housing, and
    a dosing unit arranged in at least part of the housing, the dosing unit comprising:
        a needle,
        a shield,
        a drug container comprising the drug,
        a plunger movable in the container,
        a shaft having a first position wherein the shaft is spaced from the plunger and a second position wherein the shaft contacts the plunger,
        a first mechanical power supply for supplying a first mechanical force for moving the plunger via the shaft to deliver the drug to the human body,
        an activation mechanism configured to release the first mechanical force of the first mechanical power supply, and
        a damper configured to oppose the first mechanical force as the shaft moves from the first position to the second position,
    wherein the auto-injector comprises a second mechanical power supply for supplying a second mechanical force, the auto-injector having:
        a first state in which the needle is protected from needle damage or contamination,
        a second state in which the needle is ready to penetrate the human body for dosing the drug,
        a third state in which the needle has penetrated the human body and is ready to dose, and
        a fourth state in which the shield is configured to shield the needle to avoid unintended needle sticks,
    wherein the second mechanical power supply is configured to shift state of the auto-injector from the third state to the fourth state by releasing the second mechanical force,
    wherein the second mechanical power supply is configured to moves the shield from a retracted position in the third state to a projection position in the fourth state to shield the needle.

2. A single-use auto-injector according to claim 1, wherein the second mechanical power supply is configured to moves the needle into the housing from the third state to the fourth state by moving the needle and the drug container, or the whole dosing unit, into the housing.

3. A single-use auto-injector according to claim 1, wherein the second mechanical power is generated by retracting the shield into the housing.

4. A single-use auto-injector according to claim 1, further comprising a locking element configured to lock the auto-injector in the fourth state so as to lock the needle.

5. A single-use auto-injector according to claim 1, wherein the activation mechanism is configured to activate a third mechanical force of a third mechanical power supply to project the needle from the housing.

6. A single-use auto-injector according to claim 1, wherein the activation mechanism is configured to be activated by a manual force from a user.

7. A single-use auto-injector according to claim 1, further comprising a dosing lock configured to prevent unintended activation of the dosing unit.

8. A single-use auto-injector according to claim 1, wherein the first mechanical power supply is a spiral torsion spring.

9. A single-use auto-injector according to claim 1, wherein the damper comprises a mechanical escapement mechanism, and wherein the mechanical escapement mechanism comprises an escapement gear wheel configured to engage a mechanical transfer mechanism and an anchor wheel having a mass displaced from a rotation point of the anchor wheel.

10. A single-use auto-injector according to claim 1, wherein the dosage injected into the human body is in the range of 0.25-10 ml.

11. A single-use auto-injector according to claim 1, wherein the damper comprises a mechanical escapement mechanism, and further comprising a mechanical transfer mechanism for controlling a transfer of power to the shaft, the mechanical transfer mechanism comprising a first gear wheel configured to engage the first mechanical power supply and the mechanical escapement mechanism for the transfer of the power from the first mechanical power supply to the shaft.

12. A single-use auto-injector according to claim 11, wherein the mechanical transfer mechanism comprises a shaft connected to the piston, the shaft having teeth and the teeth of the shaft configured to engage the gear wheel of the transfer mechanism.

13. A single-use auto-injector according to claim 12, wherein the shaft is bendable.

14. A single-use auto-injector for injection of a dosage of a drug into a human body, comprising:
    a housing, and
    a dosing unit arranged in at least part of the housing, the dosing unit comprising:
        a needle,
        a drug container comprising the drug,
        a plunger movable in the container,
        a shaft having a first position wherein the shaft is spaced from the plunger and a second position wherein the shaft contacts the plunger,
        a first mechanical power supply for supplying a first mechanical force for moving the plunger via the shaft to deliver the drug to the human body,
        an activation mechanism configured to release the first mechanical force of the first mechanical power supply, and
        a damper configured to oppose the first mechanical force as the shaft moves from the first position to the second position,
    wherein the auto-injector comprises a second mechanical power supply for supplying a second mechanical force, the auto-injector having:
        a first state in which the needle is protected from needle damage or contamination,
        a second state in which the needle is ready to penetrate the human body for dosing the drug,
        a third state in which the needle has penetrated the human body and is ready to dose, and
        a fourth state in which the needle is shielded to avoid unintended needle sticks,
    wherein the second mechanical power supply is configured to shift state of the auto-injector from the third state to the fourth state by releasing the second mechanical force, and wherein the second mechanical power supply is configured to moves the needle into the housing from the third state to the fourth state by moving the needle and the drug container, or the whole dosing unit, into the housing.

15. A single-use auto-injector for injection of a dosage of a drug into a human body, comprising:
a housing, and
a dosing unit arranged in at least part of the housing, the dosing unit comprising:
a needle,
a shield,
a drug container comprising the drug,
a plunger movable in the container,
a shaft having a first position wherein the shaft is spaced from the plunger and a second position wherein the shaft contacts the plunger,
a first mechanical power supply for supplying a first mechanical force for moving the plunger via the shaft to deliver the drug to the human body,
an activation mechanism configured to release the first mechanical force of the first mechanical power supply, and
a damper configured to oppose the first mechanical force as the shaft moves from the first position to the second position,
wherein the auto-injector comprises a second mechanical power supply for supplying a second mechanical force, the auto-injector having:
a first state in which the needle is protected from needle damage or contamination,
a second state in which the needle is ready to penetrate the human body for dosing the drug,
a third state in which the needle has penetrated the human body and is ready to dose, and
a fourth state in which the shield is configured to shield needle is shielded to avoid unintended needle sticks,
wherein the second mechanical power supply is configured to shift state of the auto-injector from the third state to the fourth state by releasing the second mechanical force, and
wherein the second mechanical force is generated by retracting the shield into the housing.

16. A single-use auto-injector for injection of a dosage of a drug into a human body, comprising:
a housing, and
a dosing unit arranged in at least part of the housing, the dosing unit comprising:
a needle,
a drug container comprising the drug,
a plunger movable in the container,
a shaft having a first position wherein the shaft is spaced from the plunger and a second position wherein the shaft contacts the plunger,
a first mechanical power supply for supplying a first mechanical force for moving the plunger via the shaft to deliver the drug to the human body,
an activation mechanism configured to release the first mechanical force of the first mechanical power supply, and
a damper configured to oppose the first mechanical force as the shaft moves from the first position to the second position,
wherein the auto-injector comprises a second mechanical power supply for supplying a second mechanical force, the auto-injector having:
a first state in which the needle is protected from needle damage or contamination,
a second state in which the needle is ready to penetrate the human body for dosing the drug,
a third state in which the needle has penetrated the human body and is ready to dose, and
a fourth state in which the needle is shielded to avoid unintended needle sticks,
wherein the second mechanical power supply is configured to shift state of the auto-injector from the third state to the fourth state by releasing the second mechanical force,
wherein the activation mechanism is configured to activate a third mechanical power of a third mechanical power supply to project the needle from the housing.

17. A single-use auto-injector for injection of a dosage of a drug into a human body, comprising:
a housing, and
a dosing unit arranged in at least part of the housing, the dosing unit comprising:
a needle,
a drug container comprising the drug,
a plunger movable in the container,
a shaft having a first position wherein the shaft is spaced from the plunger and a second position wherein the shaft contacts the plunger,
a first mechanical power supply for supplying a first mechanical force for moving the plunger via the shaft to deliver the drug to the human body, wherein the first mechanical power supply is a spiral torsion spring,
an activation mechanism configured to release the first mechanical force of the first mechanical power supply, and
a damper configured to oppose the first mechanical force as the shaft moves from the first position to the second position,
wherein the auto-injector comprises a second mechanical power supply for supplying a second mechanical force, the auto-injector having:
a first state in which the needle is protected from needle damage or contamination,
a second state in which the needle is ready to penetrate the human body for dosing the drug,
a third state in which the needle has penetrated the human body and is ready to dose, and
a fourth state in which the needle is shielded to avoid unintended needle sticks,
wherein the second mechanical power supply is configured to shift state of the auto-injector from the third state to the fourth state by releasing the second mechanical force.

18. A single-use auto-injector for injection of a dosage of a drug into a human body, comprising:
a housing, and
a dosing unit arranged in at least part of the housing, the dosing unit comprising:
a needle,
a drug container comprising the drug,
a plunger movable in the container,
a shaft having a first position wherein the shaft is spaced from the plunger and a second position wherein the shaft contacts the plunger,
a first mechanical power supply for supplying a first mechanical force for moving the plunger via the shaft to deliver the drug to the human body, an activation mechanism configured to release the first mechanical force of the first mechanical power supply, and
a damper configured to oppose the first mechanical force as the shaft moves from the first position to the second position,
wherein the auto-injector comprises a second mechanical power supply for supplying a second mechanical force, the auto-injector having:
a first state in which the needle is protected from needle damage or contamination,
a second state in which the needle is ready to penetrate the human body for dosing the drug,
a third state in which the needle has penetrated the human body and is ready to dose, and
a fourth state in which the needle is shielded to avoid unintended needle sticks,
wherein the second mechanical power supply is configured to shift state of the auto-injector from the third state to the fourth state by releasing the second mechanical force,
wherein the damper comprises a mechanical escapement mechanism, and further comprising a mechanical transfer mechanism for controlling a transfer of power to the shaft, the mechanical transfer mechanism comprising a first gear wheel configured to engage the first mechanical power supply and the mechanical escapement mechanism for the transfer of the power from the first mechanical power supply to the shaft.

19. A single-use auto-injector for injection of a dosage of a drug into a human body, comprising:
a housing, and
a dosing unit arranged in at least part of the housing, the dosing unit comprising:
a needle,
a drug container comprising the drug,
a plunger movable in the container,
a shaft having a first position wherein the shaft is spaced from the plunger and a second position wherein the shaft contacts the plunger,
a first mechanical power supply for supplying a first mechanical force for moving the plunger via the shaft to deliver the drug to the human body,
an activation mechanism configured to release the first mechanical force of the first mechanical power supply, and
a damper configured to oppose the first mechanical force as the shaft moves from the first position to the second position,
wherein the auto-injector comprises a second mechanical power supply for supplying a second mechanical force, the auto-injector having:
a first state in which the needle is protected from needle damage or contamination,
a second state in which the needle is ready to penetrate the human body for dosing the drug,
a third state in which the needle has penetrated the human body and is ready to dose, and
a fourth state in which the needle is shielded to avoid unintended needle sticks,
wherein the second mechanical power supply is configured to shift state of the auto-injector from the third state to the fourth state by releasing the second mechanical force,
wherein the damper comprises a mechanical escapement mechanism, and wherein the mechanical escapement mechanism comprises an escapement gear wheel configured to engage a mechanical transfer mechanism and an anchor wheel having a mass displaced from a rotation point of the anchor wheel.

* * * * *